(12) United States Patent
Yatomi

(10) Patent No.: US 6,759,041 B1
(45) Date of Patent: Jul. 6, 2004

(54) PREVENTIVES/REMEDIES FOR AUTOIMMUNE DEMYELINATING DISEASES

(75) Inventor: Takehiro Yatomi, Tokyo (JP)

(73) Assignee: Mochida Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/701,486

(22) PCT Filed: May 28, 1999

(86) PCT No.: PCT/JP99/02818

§ 371 (c)(1),
(2), (4) Date: Nov. 29, 2000

(87) PCT Pub. No.: WO99/62554

PCT Pub. Date: Dec. 9, 1999

(30) Foreign Application Priority Data

May 29, 1998 (JP) .......................................... 10-149530

(51) Int. Cl.⁷ ..................... A61K 39/395; C07K 16/00; C07K 16/18
(52) U.S. Cl. .................. 424/130.1; 530/350; 530/387.1
(58) Field of Search .......................... 424/130.1, 142.1, 424/143.1, 139.1, 144.1, 153.1, 154.1, 155.1, 156.1, 178.1, 193.1, 194.1, 195.11; 435/69.5, 70.1, 332, 69.1, 91.1; 514/2; 530/387.9, 388.15, 388.22, 388.23, 388.24, 391.1, 350, 387.15, 387.1; 536/23.1, 23.5

(56) References Cited

U.S. PATENT DOCUMENTS

| | | | | |
|---|---|---|---|---|
| 5,830,469 A | * | 11/1998 | Lynch et al. ............. | 424/143.1 |
| 6,046,310 A | * | 4/2000 | Queen et al. ............ | 530/391.1 |
| 6,098,631 A | * | 8/2000 | Holoshitz et al. ........... | 128/898 |
| 6,184,210 B1 | * | 2/2001 | Keana et al. ............ | 260/998.2 |
| 6,348,334 B1 | * | 2/2002 | Nagata et al. ........... | 435/252.3 |
| 6,358,508 B1 | * | 3/2002 | Ni et al. .................. | 424/139.1 |
| 6,399,327 B1 | * | 6/2002 | Wallach et al. .......... | 435/320.1 |
| 6,544,523 B1 | * | 4/2003 | Chu et al. ................. | 424/192.1 |

FOREIGN PATENT DOCUMENTS

| | | |
|---|---|---|
| EP | 0285883 | 10/1988 |
| EP | 0 675 200 A1 | 10/1995 |
| JP | 0675200 A1 * | 10/1995 |
| JP | 63-230629 | 9/1998 |
| WO | WO95/10540 A1 | 4/1995 |
| WO | WO9513293 | 5/1995 |
| WO | WO/97/02290 A1 | 1/1997 |
| WO | WO9702290 | 1/1997 |
| WO | WO97/03998 A1 | 2/1997 |
| WO | WO9742319 | 11/1997 |
| WO | WO 98 10070 | 3/1998 |
| WO | WO9818487 | 5/1998 |
| WO | WO99/18781 A1 | 4/1999 |

OTHER PUBLICATIONS

Kennedy et al., "Inhibition of Murine Relpsing Experimental Autoimmune Encephalomyelitis by Immune Tolerance to Proteolipid Protein and its Encephalitogenic Peptides," J. Immun., vol. 144, pp. 909–15, 909–10 (1990).*
Nicholson et al., "An Altered Peptide Ligand Mediates Immune Deviation and Prevents Autoimmune Encephalomyeliis," Immunity, vol. 3, pp. 397–405 (1995).*
Hughes and Crispe, "A Naturally Occurring Soluble Isoform of Murine Fas Generated by Alternative Splicing," J. Exp. Med, vol. 182, 1395–1401, (1995).*
Sabelko et al., "Fas and Fas Ligand Enhance the Pathogenesis of Experimental Allergic Encephalomyelitis, but are not Essential for Immune Priviliege in the Central Nervous System," J. Immun., vol. 159, pp. 3096–3099 (1997).*
Elliott et al., J. of Cinical Invest., vol. 98, No. 7 (1996) pp. 1602–1612.
Waldner et al., J. of Immuno., vol. 159, No. 7 (1997) pp. 3100–3103.
D'Souza et al., J. Exp. Med., vol. 184 (1996) pp. 2361–2370.
Sabelko et al., J. of Immuno., vol. 159, No. 7 (1997) pp. 3096–3099.
Marusic et al., J. Exp. Med., vol. 186, No. 4 (1997) pp. 507–515.
Malipiero, Ursula et al., Eur. J. Immunol., vol. 27, pp. 3151–3160 (1997).
Clark, Robert B. et al., Clinical Immunology and Immunopathology, vol. 85, No. 3, pp. 315–319 (1997).
Yoshinobu Okuda et al.; Molecular Immunology vol. 35, (1998), pp. 317–326, XP001013461.
Ruggero De Maria et al.; Immunology Today, vol. 19, No. 3, (Mar. 1, 1998), pp. 121–125, XP004108577.
Bruno Brunetti et al.; The Journal of Immunology, vol. 159, (1997) pp. 5733–5741, XP001013294.
Catherine A. White et al.; Journal of Neuroimmunology, vol. 82, (Feb. 1, 1998) pp. 47–55, XP001013297.

* cited by examiner

Primary Examiner—James Housel
Assistant Examiner—Zachariah Lucas
(74) Attorney, Agent, or Firm—Birch, Stewart, Kolasch & Birch, LLP

(57) ABSTRACT

The present invention is drawn to a method for treating autoimmune demyelinating diseases by administering to a patient in need thereof an effective amount of a Fas antagonist. The method of the present invention uses, for example, as a Fas antagonist a substance which suppresses Fas-Fas ligand binding.

8 Claims, 2 Drawing Sheets

PREVENTIVES/REMEDIES FOR AUTOIMMUNE DEMYELINATING DISEASES

This application is the national phase under 35 U.S.C. § 371 of PCT International Application No. PCT/JP99/02818 which has an International filing date of May 28, 1999, which designated the United States of America.

TECHNICAL FIELD

This invention relates to preventives and remedies for autoimmune demyelinating diseases which contain an apoptosis-suppressing substance as their effective component.

BACKGROUND ART

Fas is a cell surface protein which transmits apoptosis signal to the cell, and Fas is recognized by Fas antibody (Yonehara, S. et al., J. Exp. Med., vol. 169, 1747–1756, 1989) which is a monoclonal antibody produced by immunizing a mouse with human fibroblast. Fas gene was cloned by Itoh, N. et al., and it was then found out that Fas is a cell membrane protein of about 45 kD, and from the amino acid sequence, it was revealed that Fas is a member of TNF receptor family (Cell, vol. 66, pages 233–243, 1991). Mouse Fas gene was also cloned, and the expression of Fas mRNA in thymus, liver, lung, heart, and ovary was confirmed (Watanabe-Fukunaga, R. et al., J. Immunol., vol. 148, pages 1274–1279, 1992).

Human Fas ligand is a polypeptide which has been reported by Nagata et al. to be a native molecule which induces apoptosis of Fas-expressing cells (Takahashi, T. et al., International Immunology, vol. 6, pages 1567–1574, 1994). Human Fas ligand is a glycosilated type II membrane protein of TNF family with a molecular weight of about 40 kD. As in the case of TNF, human Fas ligand in the human body is estimated to be in the form of a trimer (Tanaka, M. et. al., EMBO Journal, vol. 14, pages 1129–1135, 1995). The extracellular domain of the human Fas ligand is highly homologous with the extracellular domain of rat Fas ligand (Suda, T. et al., Cell, vol. 75, pages 1169–1178, 1993) and mouse Fas ligand (Takahashi, T. et al., Cell, vol. 76, pages 969–976, 1994). The human Fas ligand recognizes not only the human Fas but also the mouse Fas to induce the apoptosis, and vice versa, the rat Fas ligand and the mouse Fas ligand also recognize the human Fas to induce the apoptosis.

Considerable researches have also been done on the mechanism of signal transduction in the cell upon the Fas-mediated apoptosis, and identification and cloning of the factor which interacts with the intracellular domain of the Fas, in particular, the region called "death domain" to transmit or block the signal have been reported. Possibility of the involvement of interleukin-1-converting enzyme (ICE)-related thiol proteases in the signal transduction of the Fas-mediated apoptosis has also been indicated.

Relationship of the apoptosis, in particular, the Fas-mediated apoptosis with various diseases and physiological phenomena has been recently indicated. For example, possibility has been indicated for involvement of abnormal Fas-mediated apoptosis in the death of hepatocytes in viral fulminant hepatitis, in some types of autoimmune diseases, and the like.

Possibility of the involvement of the Fas/Fas ligand system in functions other than the apoptosis, for example, in the function of inducing inflammation by acting on neutrophil has also been indicated (Kayagaki, N. et al., Rinshou Meneki (Clinical Immunology), vol. 28, pages 667–675, 1996).

Autoimmune diseases are diseases induced by the attack of autoreactive lymphocytes after responding to an autoantigen, and the disease is associated with various symptoms. The body does not exhibit any excessive immunoreaction when normal, and self-tolerance is the state established in a normal body. However, abnormality in immunomodulation mechanism invites production of antibodies against various components constituting the self and emergence of autoreactive lymphocytes. The autoreactive T cell are normally removed in thymus by apoptosis. However, when such autoreactive T cell transfers to periphery without being removed in thymus by some abnormality, they are accumulated in the periphery. Tolerance is also established for B cells, and autoreactive B cells are normally removed by apoptosis. However, when the autoreactive B cells fail to be removed by some abnormality, they are also accumulated in the periphery as in the case of the T cells. The autoimmune disease are caused by such autoreactive lymphocytes.

Autoimmune demyelinating disease is induced by an autoantibody specific to nerve system, and the disease is associated with selective destruction of the myelin and the cells constituting the myelin. Histologically, the disease is associated with disappearance of myelin, cellular infiltration in the region surrounding the vein. The disease is associated with clinical conditions of loss of sight, paresthesia, quadriplegia, and other neurologic manifestation.

Detailed etiology of the demyelinating disease is not fully found out. For example, for the demyelinating inflammation undergoing recurring remission and relapse such as multiple sclerosis include, possibility of the involvement of viral infection (Carp, R. I. et al., Prog. Med. Viol., vol. 24, pages 158–177, 1978) is indicated in addition to the involvement of autoimmunity (De Keyser, J., Neurology, vol. 38, pages 371–374, 1988).

Typical treatments which has been employed for the demyelinating disease include treatment by nonspecific immunosuppression by the use of an immunosuppressant in combination with ACTH (adrenocorticotropic hormone) (Saida K. Saishin-Igaku (Current Medicine), vol. 10, pages 1963–1971, 1991). This treatment, however, failed to exhibit prolonged effects, and moreover, this treatment is not effective for the disease of chronic, progressive type (Weiner et al., Neurology, vol. 39, pages 1143–1149, 1989). In view of such situation various treatments are currently investigated for specifically suppressing the activity of the autoimmune T cells, including the administration of T cell vaccine (Ben-Nun, A et al., Nature, vol. 292, pages 60–61, 1981) or T cell receptor vaccine (J. Immunol, vol. 152, page 2510, 1994; J. Immunol, vol. 152, page 2520, 1994), oral immunity tolerance (Science, vol. 259, page 1321, 1993), peptide analog (Immunol. Today, vol. 14, page 602–609, 1993), and administration of anti-CD4 antibody. No results with significant effectivity has so far been reported except for some of these agent (T cell receptor vaccination) wherein the effect of reducing the frequency of autoantigen-reactive T cell in the peripheral blood has been reported.

When homogenate of spinal cord is subcutaneously inoculated with Freund's complete adjuvant containing killed Mycobacterium tuberculosis, symptom of encephalomyelitis such as paralysis of hind legs is evoked in sensitive animals at 10 to 14 days after the inoculation. This is the prototype of the experimental autoimmune encephalomyelitis (EAE). This is also a typical model of autoimmune disease derived by immunizing an experimental animal with a protein antigen or a peptide from brain, and this model has been extensively investigated from old days lip as a disease model of multiple sclerosis and acute disseminated encephalomyelitis (ADEM). Analysis of EAE has brought various findings including the involvement of T cell specific to autoantigens such as myelin basic protein and proteolipid protein expressed in central nerve system (Ota, K. et al., Nature, vol. 396, pages 183–187, 1990).

Various studies have been recently conducted and reported for the relation between the multiple sclerosis and the apoptosis mediated by Fas/Fas ligand system. Sameer, D. et al. reported that they found the Fas ligand expressed in microglia cells and infiltrated T cells and the Fas expressed in oligodendrocytes, in the lesion of human multiple sclerosis (J. Exp. Med., vol. 184, pages 2361–2370, 1996). Kimberly A. et al. (J. Immunol., vol. 159, pages 3096–3099, 1997) and Hanspeter, W. et al. (J. Immunol., vol. 159, pages 3100–3103, 1997) suggested through animal experiment of multiple sclerosis using lpr and gld mouse, which are genetically deficient of the Fas and the Fas ligand, respectively, that the apoptosis mediated by the Fas/Fas ligand is involved in the multiple sclerosis. In the meanwhile, Eileen, A. et al. (J. Clin. Invest., vol. 98, pages 1602–1612, 1996) and Suzana, M. et al. (J. Exp. Med., vol. 186, pages 507–515, 1997) suggested through animal experiment of the multiple sclerosis using the same lpr and gld mouse that the apoptosis mediated by the Fas/Fas ligand is not involved in the multiple sclerosis. In other words, the relationship between the pathology of the multiple sclerosis and the apoptosis mediated by the Fas/Fas ligand system is still unknown and differently conceived depending on the investigator. In addition, efficiency of the drug delivery to brain tissue is generally low, and it is utterly unknown whether the drug which suppresses the apoptosis by the Fas/Fas ligand administered to the body can suppress the Fas/Fas ligand-mediated apoptosis in the brain tissue, and it is also unknown whether the results will be the same as those obtained in the mouse genetically deficient of the Fas or the Fas ligand.

Up until now, there is no preventive and therapeutic agent for autoimmune demyelinating diseases which acts by suppressing the apoptosis, and no therapeutic agent which binds to the Fas ligand has been reported.

DISCLOSURE OF THE INVENTION

An object of the present invention is to provide a preventive and therapeutic agent for autoimmune demyelinating diseases which acts by the novel mechanism of suppressing the apoptosis. More specifically, the present invention provides a preventive and therapeutic agent for autoimmune demyelinating diseases which contains an apoptosis-suppressing substance as its effective component and a therapeutic method wherein such agent is used.

The inventors of the present invention have conducted intensive studies on the relation between the apoptosis and the autoimmune demyelinating diseases in order to save those suffering from such diseases, and found that the pathology is improved in the model of autoimmune demyelinating diseases by the apoptosis-suppressing substance. The present invention has been completed on the bases of such finding.

Accordingly, the present invention is directed to a preventive and therapeutic agent as described below.

(1) A preventive and therapeutic agent for autoimmune demyelinating diseases containing an apoptosis-suppressing substance as its effective component.

(2) A preventive and therapeutic agent according to (1) wherein said apoptosis-suppressing substance is a Fas antagonist.

(3) A preventive and therapeutic agent according to (1) or (2) wherein said apoptosis-suppressing substance is a substance which suppresses Fas-Fas ligand binding.

(4) A preventive and therapeutic agent according to any one of (1) to (3) wherein said apoptosis-suppressing substance is a Fas derivative.

(5) A preventive and therapeutic agent according to any one of (1) to (3) wherein said apoptosis-suppressing substance is an anti-Fas ligand antibody.

(6) A preventive and therapeutic agent according to any one of (1) to (5) wherein said autoimmune demyelinating disease is a disease associated with demyelinating in central nerve system.

(7) A preventive and therapeutic agent according to any one of (1) to (5) wherein said autoimmune demyelinating disease is at least one member selected from acute disseminated encephalomyelitis and multiple sclerosis.

(8) A method for preventing and treating autoimmune demyelinating diseases wherein an apoptosis-suppressing substance is administered.

(9) Use of an apoptosis-suppressing substance in producing a pharmaceutical for preventing and/or treating autoimmune demyelinating diseases.

REST MODE FOR CARRYING OUT THE INVENTION

Figure 1:
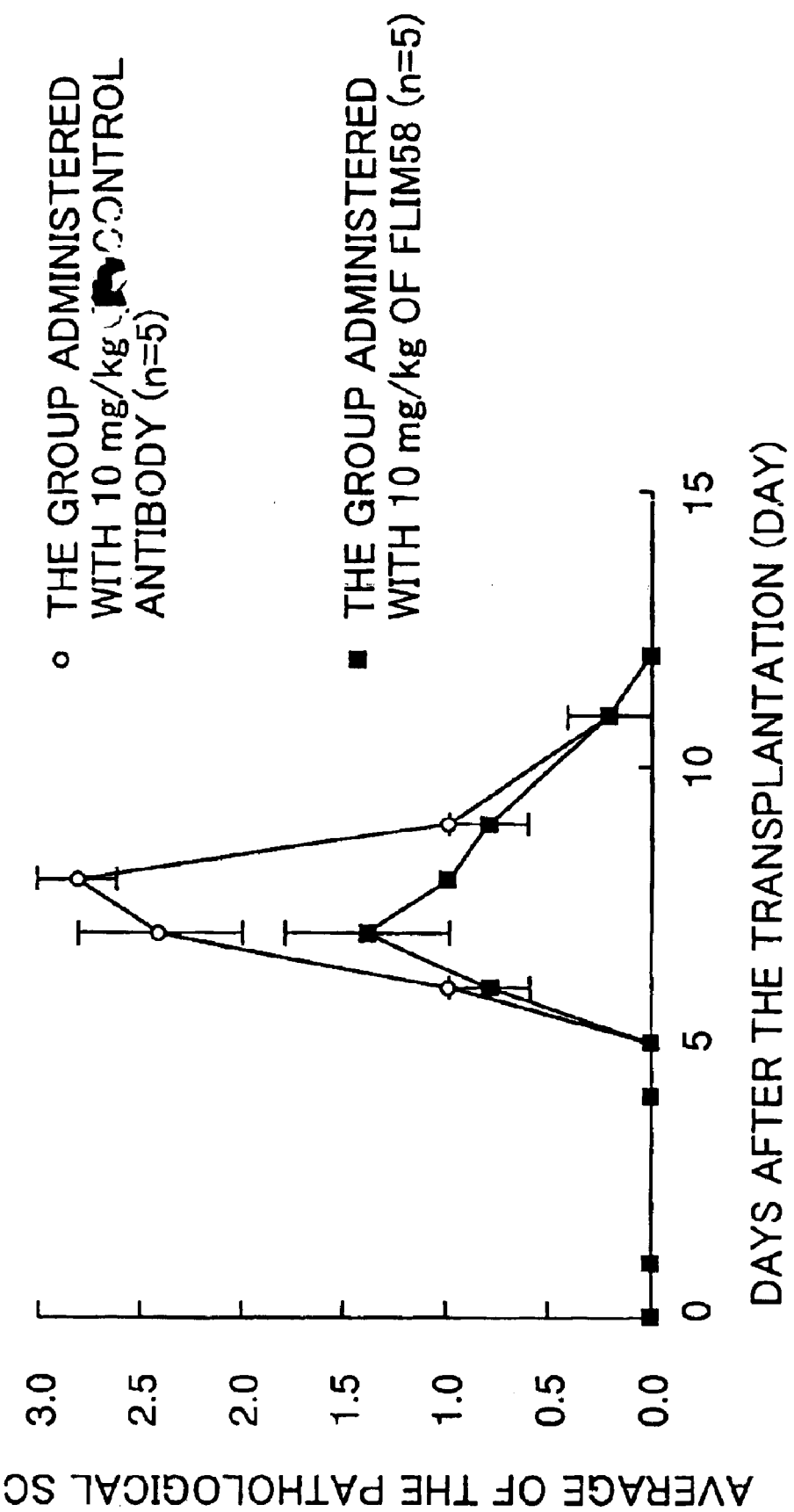
FIG. 1 is a graph showing the effect of the FLIM58 in improving the pathology of the rat EAE model.

The present invention is hereinafter described in further detail.

The autoimmune demyelinating diseases which are to be treated by the preventive and therapeutic agent of the present invention include various diseases. Such diseases may be roughly categorized into the diseases wherein the demyelination occurs in the central nervous system and the diseases wherein the demyelination occurs in the peripheral nervous system. Preferably, the diseases wherein the demyelination occurs in the central nervous system are treated by the present invention.

Typical diseases associated with the demyelination in the central nervous system are acute disseminated encephalomyelitis and multiple sclerosis and the like. The acute disseminated encephalomyelitis include idiopathic acute disseminated encephalomyelitis, post infectious acute disseminated encephalomyelitis, and post vaccinal acute disseminated encephalomyelitis and the like. Multiple sclerosis includes concentric sclerosis, neuromyelitis optica (Devic's disease), and the like. These diseases, and in particular, the multiple sclerosis undergo recurring remission and relapse. Both the disease in the remission phase and the relapse phase are to be treated by the agent of the present invention acting as a preventive agent and a therapeutic agent, respectively.

The diseases associated with the demyelination in peripheral nerve system include chronic, inflammatory demyelinating polyradiculitis and acute, inflammatory, demyelinating polyradiculitis and the like. The acute, inflammatory, demyelinating polyradiculitis includes Guillain-Barre syndrome and the like.

In these diseases, the apoptosis-suppressing substance suppresses the apoptosis occurring in each disease to realize the therapeutic effects for the disease. In the remission phase or before the emergence of the pathological condition of the disease, the apoptosis-suppressing substance suppresses the apoptosis to realize prophylactic effects for the disease.

The terms "prevention", "preventive" and "prophylactic" used in the present invention encompass both the prevention of the first occurrence of the disease and the prevention of the relapse of the disease after the remission.

It should be noted that mammals other than human may also be treated by the agent of the present invention although the human is the most important object of the therapy.

The apoptosis-suppressing substance used in the present invention is not limited to any particular type as long as it suppresses or inhibits the apoptosis.

Typical apoptosis-suppressing substances are Fas antagonists and substances which are capable of suppressing the binding between the Fas and the Fas ligand. The substance employed is not limited to any particular type as long as it blocks signal generation by the Fas or transduction of the thus generated signal at some stage to thereby suppress the function or the biological action of the Fas/Fas ligand system (and in particular, the apoptosis). The mechanism of such blockage may be inhibition of the action, function or expression of the Fas ligand or the Fas; interaction with the extracellular domain of the Fas ligand or the Fas; inhibition of the Fas ligand-Fas interaction; affecting the interaction between the intracellular domain of the Fas and the intracellular factor which interacts with the intracellular domain of the Fas; inhibition of the activity of the intracellular factor (for example, ICE-like protease) which is involved in the signal transduction of the Fas-mediated apoptosis, and the like. The apoptosis-suppressing substance may comprise either a high molecular weight protein compound or a low molecular weight compound.

Exemplary apoptosis-suppressing substances include substances which have the activity of suppressing the Fas-mediated apoptosis, such as a Fas derivative; an anti-Fas antibody; an anti-Fas ligand antibody; an antisense oligonucleotide for the gene of the Fas or the Fas ligand; an antisense oligonucleotide for the mRNA of the Fas or the Fas ligand; a substance which interacts with the intracellular domain of the Fas; and an ICE inhibitor. The apoptosis-suppressing substances used in the present invention is preferably the one which has the function of suppressing the Fas-mediated apoptosis such as Fas derivative, anti-Fas antibody, or anti-Fas ligand antibody. Furthermore, the anti-Fas antibody or the anti-Fas ligand antibody is preferably the antibody whose antigen is the Fas or the Fas ligand from the animal to be treated. For example, the anti-Fas antibody or the anti-Fas ligand antibody used for treating human is preferably the antibody whose antigen is the Fas or the Fas ligand from human, namely, anti-human Fas antibody or anti-human Fas ligand antibody.

The anti-Fas ligand antibody is preferably a chimeric antibody or a humanized antibody. An exemplary preferable chimeric antibody which may be used for treating a human is a chimeric antibody comprising the constant region from the human antibody and the variable region from a non-human antibody. An exemplary preferable humanized antibody which may be used for treating a human is a humanized antibody wherein the constant region and the framework region (FR) are of human origin, and the complementarity determining region (CDR) is of non-human origin. More preferably, the anti-Fas ligand antibody used in the present invention is a reshaped human antibody wherein the CDR from the antibody of a mammal other than human such as mouse is replaced with the CDR of the human antibody. A non-human antibody is associated with biological defects when it is used in treating a human, for example, relatively short circulation half life, lack of developing various important functional properties of the immunoglobulin, and immunogenicity. Furthermore, if various mouse monoclonal antibodies or other monoclonal antibodies with the antigenicity against human are developed in future and one or more such non-human antibodies are used for once or for several times, the subsequent administration of such non-human antibody after such initial administration may be nullified due to the crossreactivity even if the subsequent therapy had no relation to the initial therapy. In such a case, the non-human antibody administered after the initial administration may even act as a hazardous substance. The chimeric antibody and the humanized antibody have obviated such defects.

The Fas antagonist used in the present invention is preferably the one which suppresses the apoptosis of the Fas-expressing cell in an appropriate assay, for example, in the assay described in International Patent Application Publication No. WO 95/13293. This publication cited herein is incorporated herein by reference.

The antibody used in the present invention may be either a polyclonal antibody or a monoclonal antibody, and the molecular species of the antibody used in the present invention is not particularly limited. The antibody used in the present invention may be either an antibody molecule of normal form or a fragment thereof as long as the antibody used is capable of binding to the antigen to inhibit the Fas-mediated apoptosis. Exemplary antibody fragments include Fab, F(ab')$_2$, Fv, and single chain Fv (scFv) which is the Fv of heavy chain linked to the Fv of light chain by an adequate linker to form a single chain. Among these, an example of the most preferable anti-Fas ligand antibody is mouse F919-9-18 antibody produced by hybridoma F919-9-18 which was originally deposited on Jun. 22, 1995 in National Institute of Bioscience and Human Technology, Agency of Industrial Science and Technology (1–3, Higashi 1-chome, Tsukuba-shi, Ibaraki-ken, Japan) (Accession No. P-15002) and transferred from the original deposition to the international deposition on May 9, 1996 (Accession No. FERM BP-5535).

The anti-Fas ligand antibody and the anti-Fas antibody used in the present invention may be prepared by known process, for example, by the process described in International Patent Application Publication No. WO95/13293 and International Patent Application Publication No. WO97/02290. These publications are herein incorporated by reference.

The chimeric antibody which may be used in the present invention may be produced by a known chimeric antibody production process. For example, a method for producing a chimeric protein is described in Example 1 of the International Patent Application Publication No. WO 95/13293. This publication is herein incorporated by reference.

The humanized antibody used in the present invention may be prepared in accordance with Riechmann, L. et al. (Nature 332: 323 (1988) and European Patent Publication No. EP-A-0239400); Queen et al. (Proc. Natl. Acad. Sci. USA 86: 10029 (1989), International Patent Application Publication Nos. WO 90/07861 and WO 92/11018); Co et al. (Proc. Natl. Acad. Sci. USA 88: 2869 (1991)); Co et al. (Nature 351: 501 (1991)); Co et al. (J. Immunol. 148: 1149 (1992)), and the like. These publications are herein incorporated by reference. A preferable example is humanized anti-Fas ligand antibody having the CDR derived from the murine F919-9-18 antibody, which is disclosed in International Patent Application Publication No. WO 97/02290 (Application No. PCT/JP96/01820).

The Fas derivative used in the present invention is not limited to any particular type as long as it is capable of binding at least with the Fas ligand, or capable of inhibiting the Fas ligand-mediated apoptosis. The Fas derivative may also be the one which comprises an amino acid sequence of a known Fas that has been arbitrarily mutated at one or more amino acid residues by substitution, deletion or/and addition, and which inhibits the biological actions of the Fas/Fas ligand system, and in particular, the Fas-mediated apoptosis, with the binding activity to the Fas ligand retained. The Fas derivative may also comprise a mutant of Fas, Fas in a truncated form, a chimeric protein, a fusion protein, and a chemically modified Fas. The Fas from which the Fas derivative is derived may be the one derived from any animal species as long as above-mentioned property retained, although use of the Fas of human origin is preferred in consideration of the antigenicity.

Exemplary Fas derivatives are a known Fas from which the extracellular domain or the transmembrane domain has been deleted; a chimeric protein of the extracellular domain of a Fas and another protein such as human Fas-Fc (hFas-Fc) which is a chimeric protein of the extracellular domain of human Fas and Fc fragment of human immunoglobulin. The Fas derivative is not limited for its production process, and may be the one prepared by utilizing known Fas sequences and known gene engineering techniques. For example, the production process is described in the Example 1 of International Patent Application Publication No. WO 95/13293 and Examples of Application Publication No. WO 97/42319. These publications are herein incorporated by reference.

Another preferable Fas derivative is the Fas having a deletion in its N terminal. Among these, Fas derivatives, the shFas(nd29)-Fc and the shFas(nd29)-hinge (International Patent Application Publication No. WO 97/42319) coded in plasmids (pM1304 and pM1317) included in the E. coli which were originally deposited in Mar. 14, 1996 in National Institute of Bioscience and Human Technology, Agency of Industrial Science and Technology (1–3, Higashi 1-chome, Tsukuba-shi, Ibaraki-ken, Japan) (Accession Nos. P-15514 and P-15515) and transferred from the original deposition to the international deposition on Mar. 6, 1997 (Accession No. FERM BP-5854 and Accession No. FERM BP-5855) are derivatives including the extracellular domain of the known human Fas from which N terminal sequence of from 1st to 29th amino acid has been deleted, and these highly active derivatives are preferable examples of the effective component for the preventive and therapeutic agent of autoimmune demyelinating diseases of the present invention. This publication is herein incorporated by reference.

The Fas derivatives as described above which may be used in the present invention may be confirmed for their activity to bind to the Fas ligand or their activity to suppress the Fas-mediated apoptosis by an appropriate assay method.

The antisense oligonucleotide for the gene of the Fas or the Fas ligand or the antisense oligonucleotide for the mRNA of the Fas or the Fas ligand used in the present invention is not limited to any particular sequence as long as it inhibits the expression of the Fas or the Fas ligand, and may be, for example, the antisense oligonucleotide of the Fas ligand disclosed in Example 20 of International Patent Application Publication No. WO 95/13293. This publication is herein incorporated by reference.

The preventive and therapeutic agent for autoimmune demyelinating diseases of the present invention can be used as a therapeutic agent for the patients suffering from the autoimmune demyelinating diseases, and as a prophylactic agent for the autoimmune demyelinating diseases in the case of the patients suffering from systemic autoimmune disease, organ specific autoimmune disease except to nerve system, viral infection and those inoculated with a vaccine and the like diseases. Furthermore, the preventive and therapeutic agent of the present invention can be used as an agent for preventing relapse of the disease in the case of the patients suffering from multiple scleroses or other diseases wherein remission and relapse phases are repeated, and who are in the remission phase.

The preventive and therapeutic agent for autoimmune demyelinating diseases of the present invention is characterized by its inclusion of the apoptosis-suppressing substance as described above. The agent may be in the form of a pharmaceutical composition or kit wherein the Fas antagonist is appropriately combined with at least one pharmaceutical carrier or medium such as sterilized water, physiological saline, a vegetable oil, a mineral oil, a higher alcohol, a higher fatty acid, or a nontoxic organic solvent; and optional additives such as an excipient, a colorant, an emulsifier, a suspending agent, a surfactant, a solubilizer, a nonadsorptive, a stabilizer, a preservative, an antioxidative, a buffer, an isotonizing agent, or a pain relieving agent. The agent may be administered either orally, or parenterally by intravenous, intracoronary, subcutaneous, intramuscular, percutaneous, intrarectal, or topical administration or by inhalation.

Preferably, the preventive and therapeutic agent of the present invention is parenterally administered by either systemic or topical, rapid or continuous administration.

The preventive and therapeutic agent of the present invention may be administered to a human at an appropriate dose which may be determined by taking the conditions and the age of the patient as well as the administration route into consideration. For example, an adequate divided dose in the range of approximately 0.01 to 1000 mg/kg may be selected in the case of systemic administration, and within this range, an adequate divided dose in the range of 0.01 to 100 mg/kg may be preferably selected. The preventive and therapeutic agent for autoimmune demyelinating diseases of the present invention, however, is not limited to the administration route and the dose as described above. Two or more apoptosis-suppressing substance including Fas antagonists, Fas/Fas ligand binding-suppressing reagent, and anti-Fas ligand antibody may be used in combination, and in further combination with other drugs.

The preventive and therapeutic agent for autoimmune demyelinating diseases of the present invention may be formulated into a pharmaceutical preparation in a normal process. For example, an injection may be prepared by dissolving the purified apoptosis-suppressing substance such as the Fas antagonist, the Fas/Fas ligand binding-suppressing reagent or the anti-Fas ligand antibody in a medium such as physiological saline or a buffer and optionally supplementing the solution with an additive such as an anti-adsorptive. The preparation may also be in the form of a lyophilizate which is to be reconstituted before its use, and may contain any of the excipients that are generally used for facilitating the lyophilization.

The apoptosis-suppressing substance used in the preventive and therapeutic agent for autoimmune demyelinating diseases of the present invention exhibits effects of suppressing organ and tissue disorders in autoimmune demyelinating disease models, in particular, in the model of demyelinating disease wherein demyelination occurs in the central nerve system as shown in the Examples. Although the effects of suppressing organ and tissue disorders demonstrated in the Examples are the prophylactic and therapeutic effects and synergy thereof, the effects of preventing the relapse of the disease can be demonstrated by conducting the investigation in the relapse model. It should be noted that, in the Examples, an anti-mouse Fas ligand antibody is used in the demonstration of the therapeutic and prophylactic effects since the models used in the experiments are mouse models. Equivalent inhibitory effects may be expected for the anti-human Fas ligand antibody when used in human.

It should be noted that the preventive and therapeutic agent for autoimmune demyelinating diseases of the present invention exhibits no toxicity as demonstrated in the following Examples, and therefore, it can be used safely. In view of such situation, the preventive and therapeutic agent for autoimmune demyelinating diseases of the present invention is expected to exhibit prophylactic, therapeutic, or ameliorating effects for the autoimmune demyelinating diseases.

Next, the present invention is described in further detail by referring to Examples which are given by way of examples and not by way of limiting the scope of the present invention. The abbreviations used in the following description are those commonly used in the art.

The production process and the apoptosis-suppressing activity of the anti-Fas ligand antibody, humanized anti-Fas ligand antibody, and the Fas derivative of the present invention are disclosed in the Examples of International Patent Application Publication Nos. WO 97/02290 and WO 97/42319.

EXAMPLE 1

Production of Anti-mouse Fas Ligand Antibody and its Purification (1) Production of Anti-mouse Fas Ligand Antibody A plasmid containing human elongation factor (EF) promoter, and in its downstream, the gene coding for the chimeric protein prepared by fusing the extracellular (Ad) domain of mouse Fas ligand from soluble mouse Fas ligand WX2 (J. Immunology, vol. 157, pages 3918–3924, 1996) and the intracellular domain, the transmembrane domain, and a part of the extracellular domain (from N terminal to 78th amino acid) of mouse CD40 ligand was prepared (Mizushima-Nagata, Nucleic Acids Research, vol. 18, page 5322, 1990). The plasmid was transfected into the WR19L cell to obtain a recombinant cell W40LFL expressing the mouse Fas ligand on its cell membrane for use as the antigen to be administered. Armenian hamsters were used for the animals to be immunized. The Armenian hamsters were subcutaneously administered with $1 \times 10^7$ W40LFL cells mixed with Freund's complete adjuvant, and a month later, subcutaneously administered with $2 \times 10^7$ W40LFL cells suspended in PBS, and in another a month later, administered with $5 \times 10^6$ W40LFL cells suspended in PBS into their foot pads. 3 days after the administration, lymph node cells were isolated and fused with mouse myeloma cell P3-X63-Ag8-U1 (P3-U1). After selecting the hybridoma in HAT medium (hypoxanthine-aminopterin-thymidine), hybridoma FLIM58 whose supernatant had neutralizing activity for cytotoxicity of mouse Fas ligand was obtained from the survived hybridomas.

(2) Production of FLIM58 and its Purification

Hybridoma FLIM58 was cultured in serum-free medium Hybridoma-SFM (GIBCO BRL), and the culture supernatant was purified by protein A column (PROSEP-A, Bioprocessing) to obtain purified antibody FLIM58. Concentration of the protein was calculated from absorbance at 280 nm.

EXAMPLE 2

Toxicity Study of the Anti-mouse Fas Ligand Antibody FLIM58

(1) Method

Male, 8 week old DBA/1J mice and C3H/He mice (Charles River Japan) were used. The mice were administered i.v. via their tail vein with the anti-mouse Fas ligand antibody FLIM58 at a dose of 100 mg/30 ml/kg. The control group was administered i.v. via their tail vein with physiological saline at a dose of 30 ml/kg. Each groups consisted of three animals for both strains. Observation period was/ days, and body weight measurement, hematological tests (red blood cell, white blood cell, platelet), and hematobiological tests (GOT, GPT, urea nitrogen), and autopsy with naked eye were conducted.

(2) Results

The body weight increase, the hematological test values (red blood cell, white blood cell, platelet), and the hematobiological test values (GOT, GPT, urea nitrogen) of the group administered with the anti-mouse Fas ligand antibody FLIM58 were not significantly different from those of the control group. In addition, no abnormalities were observed in the group administered with the anti-mouse Fas ligand antibody FLIM58 by the autopsy with naked eye.

EXAMPLE 3

Effect of Anti-mouse Fas Ligand Antibody FLIM58 in Improving the Pathology of Rat EAE Model (Adoptive Transfer Model)

(1) Preparation of Rat Adoptive Transfer Model 10 ml of Freund's complete adjuvant containing 1 mg/ml of killed Mycobacterium tuberculosis H37Ra (manufactured by Difco Laboratories) was centrifuged at 1000 rpm for 5 minutes, and the resulting precipitate was again suspended in 1.6 ml of Freund's incomplete adjuvant (manufactured by Difco Laboratories) to prepare a complete adjuvant with higher concentration of H37Ra. Myelin basic protein from guinea pig brain (manufactured by Sigma) was dissolved in physiological saline to 2.5 mg/ml, and the solution was mixed at 1:1 with the complete adjuvant of higher killed Mycobacterium tuberculosis H37Ra concentration as described above. The mixture was emulsified using. Leur lock Hamilton gastight syringe (manufactured by Chuo-Kagaku-Kogyo) to prepare an emulsion.

A female, 11 week old Lewis rat was anesthetized by intraabdominally administering 50 mg/kg of pentobarbital (manufactured by Dainihon Pharmaceuticals), and the rat was injected into both of its hind legs (foot pads) with 0.1 ml of the emulsion as described above, respectively. At day 14 after the injection, spleen was extirpated, and the spleen was disintegrated with forceps, centrifuged, and the resulting cell precipitate was suspended in 0.017M Tris-0.747% ammonium chloride solution for selectively lying the erythrocytes. The remaining cells were washed in Hanks's solution (manufactured by Nissui Pharmaceuticals) to obtain the splenocytes. The splenocytes were inoculated at a concentration of $4 \times 10^6$ cells/ml in RPMI1640 medium (manufactured by GIBCO BRL) supplemented with 25

μg/ml myelin basic protein from guinea pig brain, 2 mM L-glutamine (manufactured by Nissui Pharmaceuticals), and 10% inactivated FBS (manufactured by JRH Bioscience), and cultured at 37° C. in the presence of 5% carbon dioxide gas for 3 days. The culture medium of the splenocytes was centrifuged at 1,000 rpm for 5 minutes, and the precipitated cells were again suspended in Hanks's solution. The splenocytes were transplanted into the abdominal cavity of female, 11 week old Lewis rat at a dose of $1.2 \times 10^7$ cells/2 ml/rat to prepare the EAE model.

(2) Administration of Anti-mouse Fas Ligand Antibody FLIM58

The rats were administered with 10 mg/kg of anti-mouse Fas ligand antibody FLIM58 at the day of splenocyte transplantation (day 0), and after 6 days from the splenocyte transplantation(day 6) i.v. via their tail vein. The control group was administered with equal dose of IgG purified from normal hamster γ-globulin (manufactured by ROCKLAND) using protein A column. Each group consisted of 5 rats.

(3) Evaluation

The effects of FLIM58 administration was evaluated by scoring the pathology in accordance with the criteria shown in Table 1, below (Experimental Neurology, vol. 151, pages 221–228, 1995).

TABLE 1

Pathological Score of Rat EAE model

| Score | Pathology |
| --- | --- |
| Score 0 | Normal |
| Score 0.5 | Incomplete paralysis in tail (The tail raised drops down at a timing earlier than the normal rat) |
| Score 1 | Complete paralysis in tail (The tail raised quickly drops down) |
| Score 2 | Paralysis in one of the hind legs |
| Score 3 | Paralysis in both of the hind legs |
| Score 4 | Dying |
| Score 5 | Dead |

(4) Results

Figure 2:
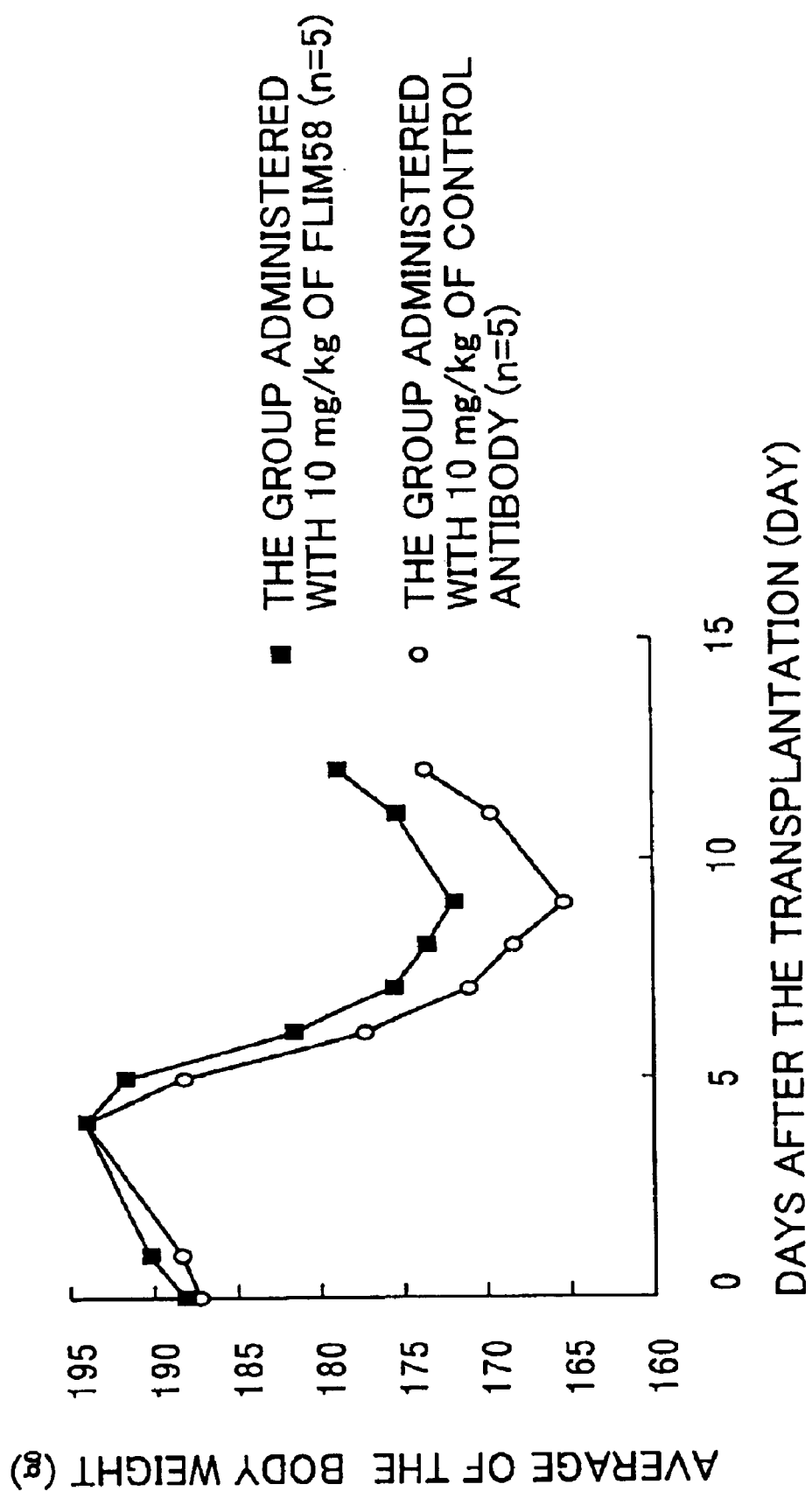
FIG. 2 is a graph showing the effect of the FLIM58 in improving the body weight loss of the rat EAE model.

The results are shown in FIGS. 1 and 2. The pathological conditions were observed at day 5 to day 6 (5 to 6 days after transplantation, hereinafter the same abbreviations are used), and after day 6, the conditions of the FLIM58 administrated group were less severe compared to the control group. The loss of body weight associated with onset of the pathology started from day 4 to day 5, and after day 5, the weight loss of the FLIM58 administrated group was less than that of the control group.

EXAMPLE 4

Effect of Anti-mouse Fag Ligand Antibody FLIM58 in Improving the Pathology of Rat EAE Model (Active Immunization Model)

(1) Preparation of Rat Actively Immunization Model

The procedure of Example 3 was repeated to produce the 1:1 emulsion of myelin basic protein and Freund's complete adjuvant. The emulsion was administered to both foot pads of the rat at a dose of 0.1 ml/foot pad (0.2 ml/rat) under anesthetization.

(2) Administration of Anti-mouse Fas Ligand Antibody FLIM58

The rats were administered with 10 mg/kg of anti-mouse Fas ligand antibody FLIM58 7 days after myelin basic protein (day 7) i.v. via their tail vein. The control group was administered with equal dose of IgG purified from normal hamster γ-globulin. Each group consisted of 5 rats.

(3) Evaluation

The effects of FLIM58 administration was evaluated by scoring the pathology in accordance with the criteria shown in Table 1.

(4) Results

The pathological conditions started at day 10, and the conditions of the FLIM58 administrated group were less severe compared to the control group.

Industrial Applicability

The preventive and therapeutic agent for autoimmune demyelinating diseases of the present invention contains an apoptosis-suppressing substance a its effective component, and it has the action of suppressing the apoptosis. Therefore, the agent of the present invention has the effects of preventing or treating the autoimmune demyelinating diseases wherein apoptosis such as the biological actions related with Fas/Fas ligand system is involved. Exemplify such biological actions is Fas-mediated cell death. The apoptosis-suppressing substance of the present invention is highly expected for use as a prophylactic and therapeutic agent for the autoimmune demyelinating diseases wherein apoptosis such as the Fas-mediated cell death is involved.

What is claimed is:

1. A method for treating autoimmune demyelinating diseases which comprises administering to a patient in need thereof an effective amount of a Fas antagonist, which is a substance that binds to Fas ligand and inhibits Fas-Fas ligand binding and suppresses apoptosis, in myelin sheath cells.

2. The method according to claim 1 wherein said Fas antagonist is an anti-Fas ligand antibody.

3. The method according to claim 1 wherein said autoimmune demyelinating disease is a disease associated with demyelination in central nervous system.

4. The method according to claim 1 wherein said autoimmune demyelinating disease is at least one member selected from acute disseminated encephalomyelitis and multiple sclerosis.

5. A method of treating a disease associated with demylination in the central nervous system which comprises administering to a patient in need thereof, an effective amount of an anti-Fas ligand antibody.

6. A method of treating multiple sclerosis which comprises administering to a patient in need thereof an effective amount of an anti-Fas ligand antibody.

7. A method of treating a disease associated with demylination in the central nervous system which comprises suppressing apoptosis with an effective amount of an anti-Fas ligand antibody.

8. A method of treating multiple sclerosis which comprises suppressing apoptosis with an effective amount of an anti-Fas ligand antibody.

* * * * *